(12) United States Patent
Fukuda et al.

(10) Patent No.: US 10,509,048 B2
(45) Date of Patent: Dec. 17, 2019

(54) BLOOD TEST APPARATUS

(71) Applicant: NIHON KOHDEN CORPORATION, Shinjuku-ku, Tokyo (JP)

(72) Inventors: Hiroyuki Fukuda, Tokyo (JP); Ryoko Nakayama, Tokyo (JP); Rikiya Tanabe, Tokyo (JP); Hyuga Masu, Tokyo (JP); Kazuhiro Emi, Tokyo (JP); Noriyoshi Hayashi, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 138 days.

(21) Appl. No.: 15/573,015

(22) PCT Filed: May 11, 2016

(86) PCT No.: PCT/JP2016/002310
§ 371 (c)(1),
(2) Date: Nov. 9, 2017

(87) PCT Pub. No.: WO2016/181651
PCT Pub. Date: Nov. 17, 2016

(65) Prior Publication Data
US 2018/0136244 A1 May 17, 2018

(30) Foreign Application Priority Data
May 13, 2015 (JP) .................. 2015-098402

(51) Int. Cl.
*G01N 35/00* (2006.01)
*G01N 33/48* (2006.01)

(52) U.S. Cl.
CPC ....... *G01N 35/00732* (2013.01); *G01N 33/48* (2013.01); *G01N 2035/0091* (2013.01);
(Continued)

(58) Field of Classification Search
CPC ............. G01N 35/00732; G01N 33/48; G01N 2035/00772; G01N 2035/00801; G01N 2035/0091
See application file for complete search history.

(56) References Cited

U.S. PATENT DOCUMENTS

2008/0299007 A1 12/2008 Noguchi et al.
2010/0223556 A1 9/2010 Wakabayashi et al.
(Continued)

FOREIGN PATENT DOCUMENTS

CN 101315389 A 12/2008
CN 102405414 A 4/2012
(Continued)

OTHER PUBLICATIONS

International Search Report issued in Patent Application No. PCT/JP2016/002310 dated Aug. 19, 2016.
(Continued)

*Primary Examiner* — Randy W Gibson
*Assistant Examiner* — Gedeon M Kidanu
(74) *Attorney, Agent, or Firm* — Pearne & Gordon LLP

(57) ABSTRACT

A first rack of a first color and a second rack of a second color respectively hold blood collecting tubes. After a test is finished, the first and second racks are disposed at a carrying-out section. A result screen showing a test result includes a first region of the first color and a second region of the second color. The first and second regions are displayed in positions corresponding to positions of the first and second racks in the carrying-out section. First symbols are displayed in the first region at positions corresponding to positions of the blood collecting tubes held in the first rack. Second symbols are displayed in the second region at positions corresponding to positions of the blood collecting tubes held in the second rack. A displayed appearance of each of the
(Continued)

first and second symbols is changed in accordance with the test result.

14 Claims, 5 Drawing Sheets

(52) U.S. Cl.
CPC .............. *G01N 2035/00772* (2013.01); *G01N 2035/00801* (2013.01)

(56) References Cited

U.S. PATENT DOCUMENTS

| | | | |
|---|---|---|---|
| 2011/0070126 A1 | 3/2011 | Galiano | |
| 2011/0290040 A1* | 12/2011 | Tatsutani | G01N 35/026 73/863.01 |
| 2012/0036944 A1* | 2/2012 | Chida | G01N 35/00613 73/863.01 |
| 2013/0009988 A1 | 1/2013 | Tokunaga et al. | |
| 2014/0093438 A1 | 4/2014 | Yanez et al. | |
| 2014/0157859 A1* | 6/2014 | Darmstadt | G01N 35/00693 73/1.02 |
| 2014/0256050 A1* | 9/2014 | Tanaka | G01N 35/026 436/47 |

FOREIGN PATENT DOCUMENTS

| | | |
|---|---|---|
| EP | 2 423 689 A1 | 2/2012 |
| JP | S59-116046 A | 7/1984 |
| JP | H07-018266 U | 3/1995 |
| JP | 2003-294768 A | 10/2003 |
| JP | 2004-148036 A | 5/2004 |
| JP | 2010-181197 A | 8/2010 |
| JP | 2011-247778 A | 12/2011 |
| JP | 2012-083371 A | 4/2012 |
| JP | 2014-173952 A | 9/2014 |
| WO | 2007-086140 A1 | 8/2007 |
| WO | 2010-122718 A1 | 10/2010 |
| WO | 2011-037069 A1 | 3/2011 |

OTHER PUBLICATIONS

Written Opinion issued in Patent Application No. PCT/JP2016/002310 dated Aug. 19, 2016.
Nihon Kohden Corporation "Automatic hematology analyzer MEK-8222 Celltac F", Jan. 18, 2016, Referenced in Specification.
Japanese Office Action issued in Patent Application No. JP-2015-098402 dated Jan. 15, 2019.
Chinese Office action issued in Patent Application No. 201680027744.X dated Aug. 23, 2019.

* cited by examiner

BLOOD TEST APPARATUS

TECHNICAL FIELD

The present invention relates to a blood test apparatus.

BACKGROUND ART

In Non-Patent Literature 1, an automatic hematology analyzer is disclosed as an example of a blood test apparatus. The automatic hematology analyzer is provided with a rack stand. A plurality of blood collecting tubes containing blood specimens which are collected from a plurality of subjects respectively are first received in racks. The racks holding the tubes are set in the rack stand. To start automatic measurement, the racks on the rack stand are conveyed to a test section inside the apparatus. In the test section, the blood specimens are sucked from the blood collecting tubes respectively, and numerical values as to the numbers of blood corpuscles in the blood specimens respectively are measured. Test results are managed in association with identification information items of the subjects attached as barcodes to the blood collecting tubes respectively. The identification information items can be also read by the apparatus automatically. When the apparatus fails in reading any of the identification information items, a measurement error is outputted.

When the measurement is completed, the racks are conveyed to the rack stand. A user such as a laboratory technician extracts a blood collecting tube containing a blood specimen falling out of a hematologic clinical criterion range (or a facility criterion range) from one of the racks based on the test result, and then retests the blood specimen using a microscope etc. When a measurement error is outputted, the user extracts the blood collecting tube containing the blood specimen from the rack, and uses a blood test apparatus to apply automatic testing to the blood specimen again. The blood collecting tube which should be provided for retesting is specified through visual recognition of the user.

CITATION LIST

Non Patent Literature

[NPL 1] Attached Document "Automatic hematology analyzer MEK-8222 Celltac F", Nihon Kohden Corporation, Jan. 18, 2006

SUMMARY OF INVENTION

Technical Problem

An object of the invention is to improve efficiency of work for specifying any blood specimen required for retesting, after completion of automatic testing.

Solution to Problem

In order to achieve the above object, according to one aspect of the invention, there is provided a blood test apparatus comprising:

a first rack presenting a first color, and configured to hold a plurality of blood collecting tubes;

a second rack presenting a second color which is different from the first color, and configured to hold a plurality of blood collecting tubes;

a test section configured to perform a predetermined test with respect to blood specimens contained in the blood collecting tubes;

a carry-out section at which the first rack and the second rack are disposed after the test is finished; and a display section configured to display a result screen showing a result of the test, wherein the test screen includes:

a first region displayed in a position corresponding to a position of the first rack in the carry-out section, and presenting the first color;

a second region displayed in a position corresponding to a position of the second rack in the carry-out section, and presenting the second color;

a plurality of first symbols displayed in the first region at positions corresponding to positions of the blood collecting tubes held in the first rack; and a plurality of second symbols displayed in the second region at positions corresponding to positions of the blood collecting tubes held in the second rack; and wherein a displayed appearance of each of the first symbols and the second symbols is changed in accordance with the result of the test.

According to the above configuration, a plurality of blood collecting tubes are held in a plurality of racks presenting different colors from one another. In order to show test results performed by the test section, the result screen displayed on the display section includes a plurality of regions presenting colors corresponding to the colors of the racks. Further, each of the display regions includes a plurality of symbols which are disposed so as to correspond to the positions of the blood collecting tubes held in each of the racks. A displayed appearance for each of the symbols changes in accordance with the test result. That is, the correspondence between the position of the symbol indicating each of the blood collecting tubes on the result screen and the position of each of the blood collecting tubes actually held in any of the racks can be made visually distinct through use of the colors. Thus, the user can easily specify blood collecting tubes containing blood specimens required for retesting while checking the colors on the result screen with the colors of the actual racks. Accordingly, it is possible to improve efficiency of the work for specifying the specimens required for retesting after completion of automatic testing.

DESCRIPTION OF EMBODIMENTS

Figure 1:
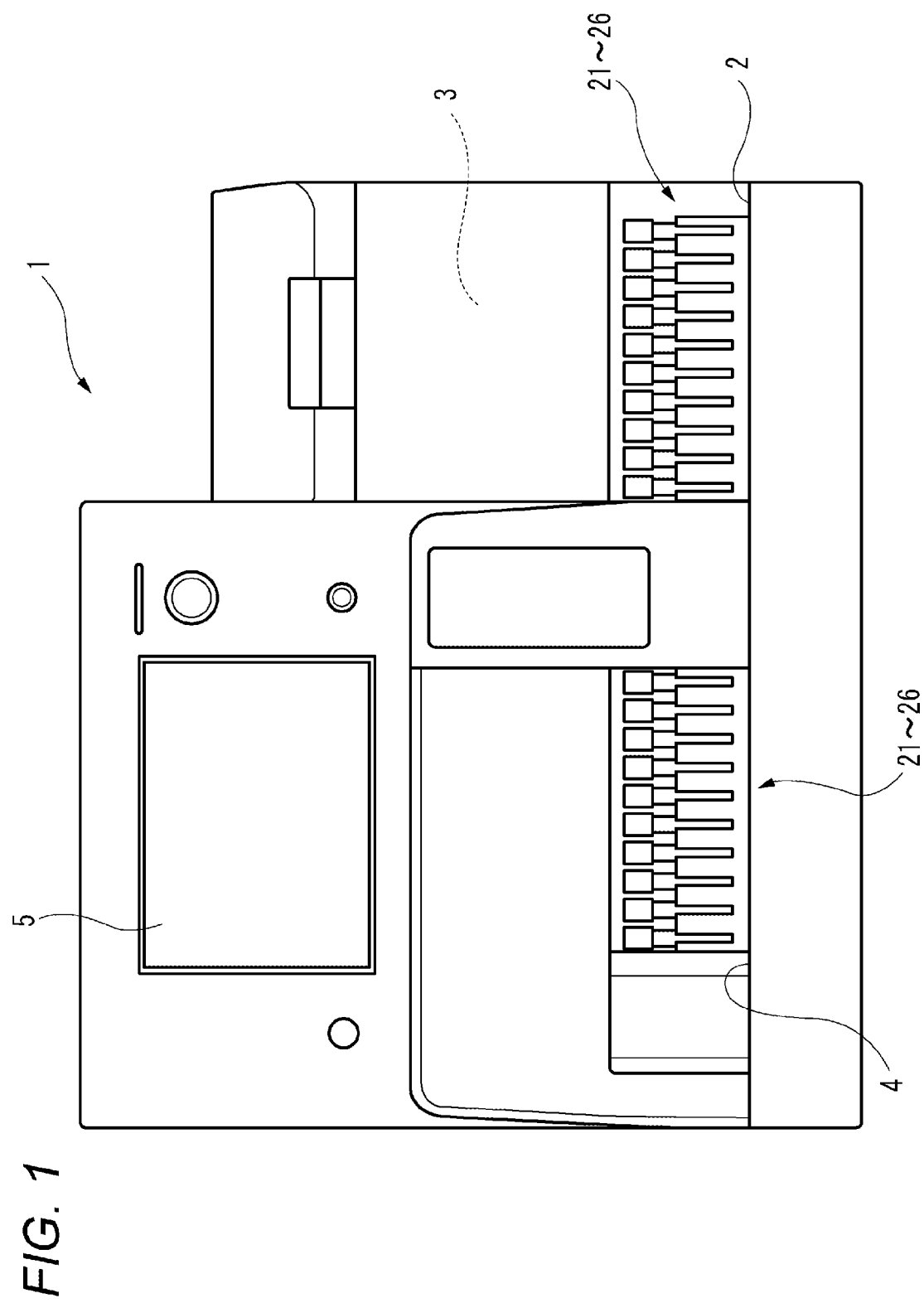
FIG. 1 schematically illustrates the external appearance of a hematology analyzer according to one embodiment.

With reference to the accompanying drawings, examples of embodiments will be described below in detail. FIG. 1 schematically illustrates external appearance of a hematology analyzer 1 (one example of a blood test apparatus) according to one embodiment. The hematology analyzer 1 comprises a carry-in section 2, a test section 3, a carry-out section 4, and a display section 5.

The carry-in section 2 is configured to support a plurality of racks. In this embodiment, the carry-in section 2 is configured to be able to support a first rack 21, a second rack 22, a third rack 23, a fourth rack 24, a fifth rack 25, and a sixth rack 26.

Figure 2:
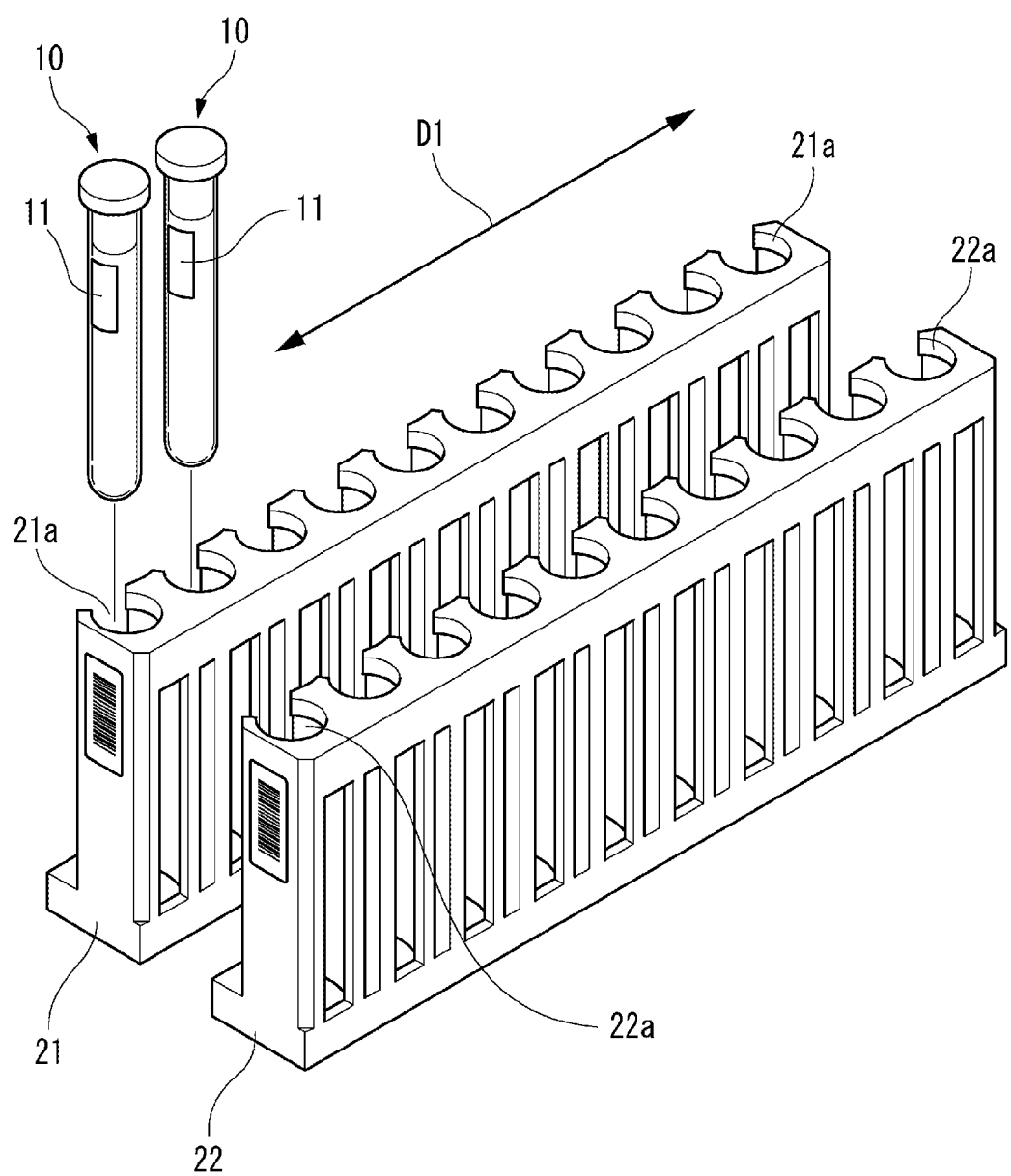
FIG. 2 illustrates the external appearances of a plurality of racks used with the hematology analyzer.

FIG. 2 representatively illustrates the external appearance of the first rack 21 and the external appearance of the second rack 22. The first rack 21 presents a first color. The first rack 21 is provided with ten holders 21a arrayed in a first direction indicated by arrows D1 in FIG. 2. Each of the holders 21a is configured to be able to hold a blood collecting tube 10. Accordingly, the first rack 21 is configured to be able to hold ten blood collecting tubes 10 which are arrayed in the first direction D1.

The second rack 22 presents a second color different from the first color. The second rack 22 is provided with ten holders 22a which are arrayed in the first direction D1. Each of the holders 22a is configured to be able to hold a blood collecting tube 10. Accordingly, the second rack 22 is configured to be able to hold the ten blood collecting tubes 10 which are arrayed in the first direction D1.

As shown in FIG. 2, an identifier 11 is attached to each of the blood collecting tubes 10. The identifier 11 includes an identification information item of a subject from which a blood specimen contained in the blood collecting tube 10 has been collected. Examples of the identifier 11 include a barcode label, and an RFID tag.

The test section 3 is provided within the hematology analyzer 1. When a user issues an instruction to execute testing, the first rack 21, the second rack 22, the third rack 23, the fourth rack 24, the fifth rack 25 and the sixth rack 26 which are supported by the carry-in section 2 are conveyed sequentially to the test section 3 by an automatic conveyance mechanism. The test section 3 is configured to automatically execute predetermined testing on the blood specimen contained in each of the blood collecting tubes 10. Since the operation per se of the test section 3 is well known, detailed description thereof will be omitted.

In addition, the test section 3 is configured to automatically read the identification information item included in the identifier 11 provided in each of the blood collecting tubes 10. A test result of the blood specimen held in the blood collecting tube 10 is managed in association with the read identification information item.

When the testing is completed, the first rack 21, the second rack 22, the third rack 23, the fourth rack 24, the fifth rack 25 and the sixth rack 26 are disposed in the carry-out section 4.

Figure 3A:
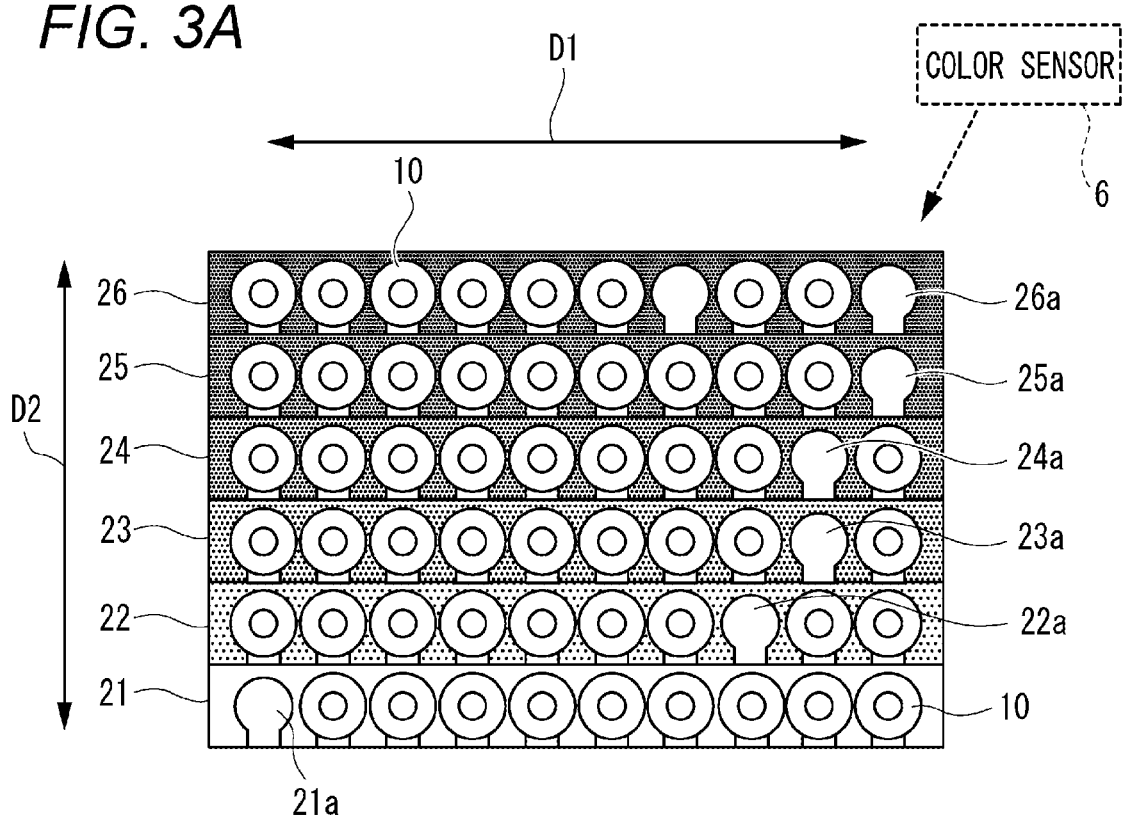
FIG. 3A explanatorily illustrates a result screen displayed on the hematology analyzer.

FIG. 3A illustrates a top view of the external appearances of the first rack 21, the second rack 22, the third rack 23, the fourth rack 24, the fifth rack 25 and the sixth rack 26 which are disposed in the carry-out section 4. In this embodiment, the first rack 21, the second rack 22, the third rack 23, the fourth rack 24, the fifth rack 25 and the sixth rack 26 are supported by the carry-out section 4 so as to be arrayed in a second direction indicated by arrows D2 in FIG. 3A. In this embodiment, the second direction D2 is perpendicular to the first direction D1 in relation to a front/rear direction of the hematology analyzer 1.

The third rack 23 presents a third color and is provided with ten holders 23a arrayed in the first direction. The fourth rack 24 presents a fourth color and is provided with ten holders 24a arrayed in the first direction. The fifth rack 25 presents a fifth color and is provided with ten holders 25a arrayed in the first direction. The sixth rack 26 presents a sixth color and is provided with ten holders 26a arrayed in the first direction.

In this embodiment, the first to sixth colors are all different colors from one another. However, a combination of the first to sixth colors may be determined suitably as long as the combination includes at least two colors. For example, the combination of colors may be determined so that the first rack 21, the third rack 23 and the fifth rack 25 present blue and the second rack 22, the fourth rack 24 and the sixth rack 26 present red.

The display section 5 is configured to display a result screen 51 showing test results performed by the test section 3. B illustrates an example of the result screen 51. The result screen 51 includes a first region 511, a second region 512, a third region 513, a fourth region 514, a fifth region 515, and a sixth region 516.

The first region 511 is displayed in a position corresponding to the position of the first rack 21 in the carry-out section 4. The first region 511 presents the first color which is the color of the first rack 21. The first region 511 includes ten first symbols 511a. The ten first symbols 511a are displayed in positions corresponding to the ten blood collecting tubes 10 held in the first rack 21.

The second region 512 is displayed in a position corresponding to the position of the second rack 22 in the carry-out section 4. The second region 512 presents the second color which is the color of the second rack 22. The second region 512 includes ten second symbols 512a. The ten second symbols 512a are displayed in positions corresponding to the ten blood collecting tubes 10 held in the second rack 22.

The third region 513 is displayed in a position corresponding to the position of the third rack 23 in the carry-out section 4. The third region 513 presents the third color which is the color of the third rack 23. The third region 513 includes ten third symbols 513a. The ten third symbols 513a are displayed in positions corresponding to the ten blood collecting tubes 10 held in the third rack 23.

The fourth region 514 is displayed in a position corresponding to the position of the fourth rack 24 in the carry-out section 4. The fourth region 514 presents the fourth color which is the color of the fourth rack 24. The fourth region 514 includes ten fourth symbols 514a. The ten fourth symbols 514a are displayed in positions corresponding to the ten blood collecting tubes 10 held in the fourth rack 24.

The fifth region 515 is displayed in a position corresponding to the position of the fifth rack 25 in the carry-out section 4. The fifth region 515 presents the fifth color which is the color of the fifth rack 25. The fifth region 515 includes ten fifth symbols 515a. The ten fifth symbols 515a are displayed in positions corresponding to the ten blood collecting tubes 10 held in the fifth rack 25.

The sixth region 516 is displayed in a position corresponding to the position of the sixth rack 26 in the carry-out section 4. The sixth region 516 presents the sixth color which is the color of the sixth rack 26. The sixth region 516 includes ten sixth symbols 516a. The ten sixth symbols 516a are displayed in positions corresponding to the ten blood collecting tubes 10 held in the sixth rack 26.

A displayed appearance of each of the ten first symbols 511a, the ten second symbols 512a, the ten third symbols 513a, the ten fourth symbols 514a, the ten fifth symbols 515a and the ten sixth symbols 516a changes in accordance with a result of automatic testing performed by the test section 3. When, for example, a test result indicates that a blood specimen falls out of a hematologic clinical criterion range (or a facility criterion range), a character "P" indicating positive is displayed in the symbol corresponding to the position of the blood collecting tube 10 containing the blood specimen.

In the illustrated example, the character "P" is displayed in each of the first symbol 511a corresponding to the blood collecting tube 10 held as the fifth from the left of the first rack 21, the third symbol 513a corresponding to the blood collecting tube 10 held as the eighth from the left of the third rack 23, the fourth symbol 514a corresponding to the blood collecting tube 10 held as the tenth from the left of the fourth rack 24, and the sixth symbol 516a corresponding to the blood collecting tube 10 held as the third from the left of the sixth rack 26.

When test result indicates that a blood specimen falls within the hematologic clinical criterion range (or the facility criterion range), display of the symbol corresponding to the position of the blood collecting tube 10 containing the blood specimen does not change. However, a character "N" expressing negative may be displayed in the symbol.

When the testing is completed, the first rack 21, the second rack 22, the third rack 23, the fourth rack 24, the fifth rack 25 and the sixth rack 26 are disposed in the carry-out section 4. A user checks the result screen 51, and extracts the blood collecting tubes 10 corresponding to the symbols in which the character "P" is displayed. The blood specimens contained in the extracted blood collecting tubes 10 are provided for retesting using a microscope etc.

In order to avoid erroneous pickup of any blood specimen, it is necessary to carefully specify the blood collecting tubes 10 provided for retesting. However, the blood collecting tubes 10 provided for testing have the same external appearances. Work for picking up some specific blood collecting tubes 10 from a large number of blood collecting tubes 10 which are arranged side by side would be a burden on the user.

According to the configuration of this embodiment, a plurality of blood collecting tubes 10 are held in a plurality of racks presenting different colors from one another. In order to show test results performed by the test section 3, the result screen 51 displayed on the display section 5 includes a plurality of regions presenting colors corresponding to the colors of the racks. Further, each of the display regions includes a plurality of symbols which are disposed so as to correspond to the positions of the blood collecting tubes 10 held in each of the racks. A displayed appearance for each of the symbols changes in accordance with the test result. That is, the correspondence between the position of the symbol indicating each of the blood collecting tubes 10 on the result screen 51 and the position of each of the blood collecting tubes 10 actually held in any of the racks can be made visually distinct through use of the colors. Thus, the user can easily specify blood collecting tubes 10 containing blood specimens required for retesting while checking the colors on the result screen 51 with the colors of the actual racks. Accordingly, it is possible to improve efficiency of the work for specifying the specimens required for retesting after completion of automatic testing.

The test results obtained from the test section 3 may include measurement errors in addition to the aforementioned results as to whether each of the blood specimens is positive or negative. The measurement errors can be further classified into two types. One type is an error caused by a fault of the test section 3. The other type is an error caused by a fault of the identification information item included in the identifier 11 attached to each blood collecting tube 10. An example of the former error includes malfunction or failure of the test section 3. An example of the latter error includes detachment of the identifier 11. Or when the identifier 11 is a barcode label, the latter error may be caused by stains or scratches of the barcode.

Figure 3B:
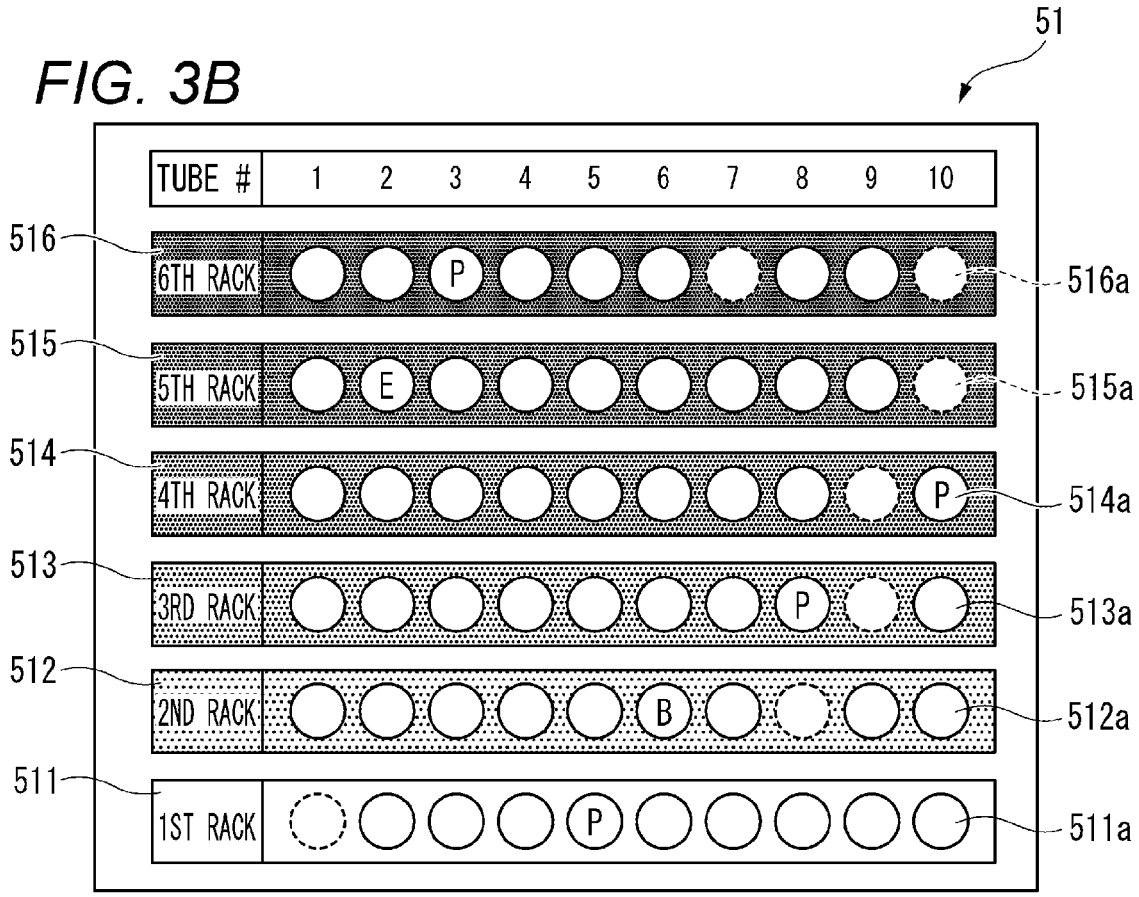
FIG. 3B explanatorily illustrates a result screen displayed on the hematology analyzer.

As shown in FIG. 3B, the result screen 51 contains a character "E" and a character "B". The character "E" is displayed in the case where the test result indicates that the measurement error is caused by the fault of the test section 3. In the illustrated example, the character "E" is displayed in the fifth symbol 515a corresponding to the blood collecting tube 10 held as the second from the left of the fifth rack 25. The character "B" is displayed in the case where the test result indicates that the measurement error is caused by the fault of the identifier 11. In the illustrated example, the character "B" is displayed in the second symbol 512a corresponding to the blood collecting tube 10 held as the sixth from the left of the second rack 22.

According to such a configuration, the user can easily specify blood collecting tubes 10 containing the blood specimen required for remeasurement while checking the colors on the result screen 51 and the colors of the actual racks. Accordingly, it is possible to further improve the efficiency of the work for specifying specimens required for retesting after completion of automatic testing.

Particularly in the case of the configuration in which it can be displayed whether the measurement error is caused by the test section 3 or by the identifier 11, the user can easily judge which to adjust the test section 3 or the identifier 11 while referring to the display. Accordingly, it is possible to further improve the efficiency of the work for specifying specimens required for retesting after completion of automatic testing.

Each first symbol 511a, each second symbol 512a, each third symbol 513a, each fourth symbol 514a, each fifth symbol 515a and each sixth symbol 516a may be configured so that the displayed appearance for each of the first to sixth symbols 511a to 516a can change in accordance with whether the blood collecting tube 10 is held or not in the corresponding position in the first rack 21, the second rack 22, the third rack 23, the fourth rack 24, the fifth rack 25 or the sixth rack 26.

In the illustrated example, the first symbol 511a corresponding to the blood collecting tube 10 held as the first from the left of the first rack 21, the second symbol 512a corresponding to the blood collecting tube 10 held as the eighth from the left of the second rack 22, the third symbol 513a corresponding to the blood collecting tube 10 held as the ninth from the left of the third rack 23, the fourth symbol 514a corresponding to the blood collecting tube 10 held as the ninth from the left of the fourth rack 24, the fifth symbol 515a corresponding to the blood collecting tube 10 held as the tenth from the left of the fifth rack 25, and the sixth symbols 516a corresponding to the blood collecting tubes 10 held as the seventh and the ninth from the left of the sixth rack 26 are paled out. As apparent from comparison with in FIG. 3A, the display can indicate that the blood collecting tubes 10 are not held in the holders in the corresponding positions.

When a large number of blood collecting tubes 10 are arrayed, any place where a blood collecting tube 10 is absent can be recognized as a characteristic point. According to the aforementioned configuration, absence of the blood collecting tube 10 in the actual rack is reflected on the result screen 51 while keeping its positional relationship of the present blood collecting tubes 10. Therefore, it is possible to easily specify blood collecting tubes 10 containing blood specimens required for retesting. Accordingly, it is possible to further improve the efficiency of the work for specifying the specimens required for retesting after completion of automatic testing.

As shown in FIG. 1, the carry-out section 4 in which the first rack 21, the second rack 22, the third rack 23, the fourth rack 24, the fifth rack 25 and the sixth rack 26 which have been tested by the test section 3 are disposed is disposed adjacent to the display section 5 in an up/down direction of the hematology analyzer 1.

According to such a configuration, when it is performed the work for picking up blood collecting tubes 10 containing specimens required for retesting from the racks, the user can compare the result screen 51 with the states of the actual first rack 21, the actual second rack 22, the actual third rack 23, the actual fourth rack 24, the actual fifth rack 25 and the actual sixth rack 26 easily with his/her eyes. Accordingly, it is possible to further improve the efficiency of the work for specifying the specimens required for retesting after completion of automatic testing.

As long as the result screen 51 and the arrays of the actual blood collecting tubes 10 can be laid adjacently to each other so that they can easily compared with each other, the positional relationship between the display section 5 and the carry-out section 4 may be determined appropriately. For example, the display section 5 and the carry-out section 4 may be disposed to be adjacent to each other in the up/down direction of the hematology analyzer 1.

The display section 5 has a configuration in which when a predetermined operation is given to at least one of the ten first symbols 511a, the ten second symbols 512a, the ten third symbols 513a, the ten fourth symbols 514a, the ten fifth symbols 515a, and the ten sixth symbols 516a, the display section 5 displays detailed information of the blood specimen contained in the blood collecting tube 10 corresponding to the operated symbol.

Figure 4A:
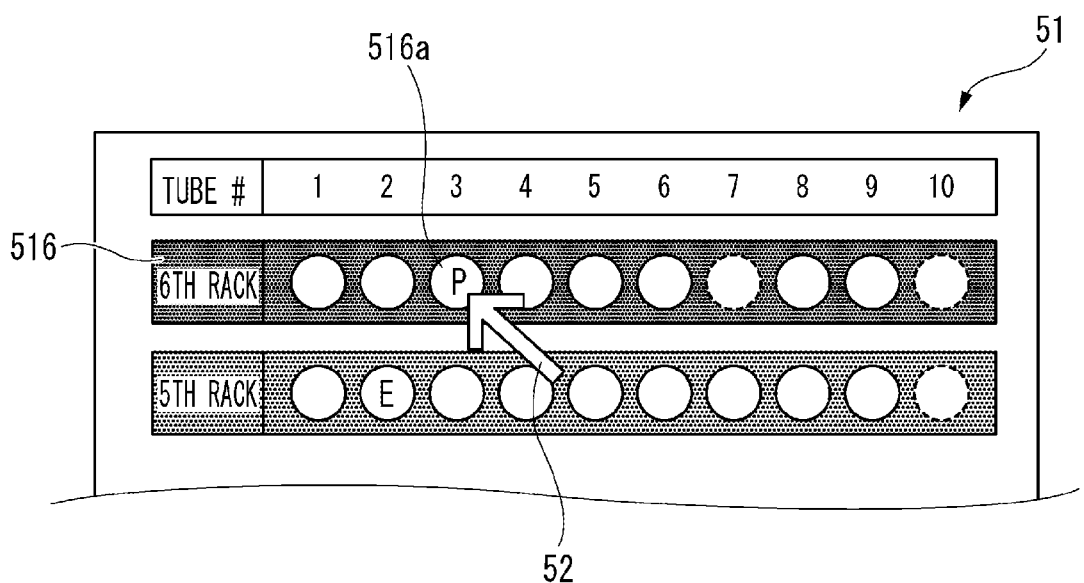
FIG. 4A explanatorily illustrates a result screen displayed on the hematology analyzer.
Figure 4B:
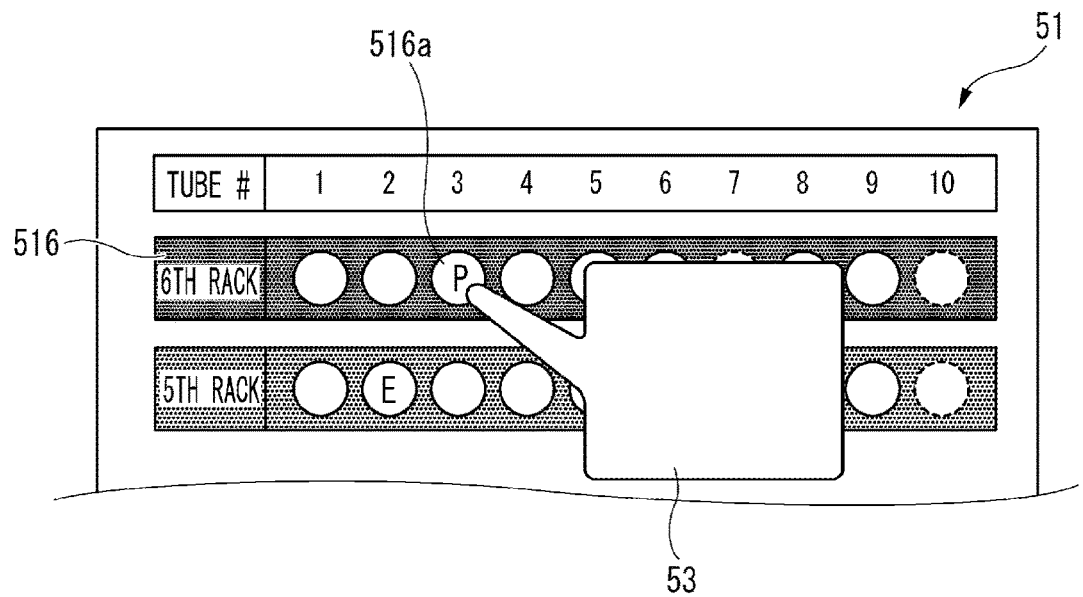
FIG. 4B explanatorily illustrates a result screen displayed on the hematology analyzer.

For example, as shown in FIG. 4A, a cursor 52 is displayed on the result screen 51. The cursor 52 is configured to move on the result screen 51 by an input device such as a mouse so as to be able to operate any symbol. In the illustrated example, the cursor 52 is disposed on the sixth symbol 516a corresponding to the blood collecting tube 10 which is held as the third from the left of the sixth rack 26. When an operation input such as click is performed in this state, detailed information 53 of the blood specimen contained in the blood collecting tube 10 corresponding to the sixth symbol 516a is displayed as shown in FIG. 4B. Examples of the detailed information include the identification information item of the subject from which the blood specimen has been collected, detailed numerical value data of the test result, etc. That is, the identification information item stored in the identifier 11 and read by the test section 3 or the test data acquired by the test section 3 can be used for displaying the detailed information 53.

According to such a configuration, the user can acquire detailed information of a blood specimen held in a desired blood collecting tube 10 on the result screen 51 if necessary during work for specifying blood collecting tubes 10 required for retesting. Accordingly, it is possible to further improve the efficiency of the work for specifying the specimens required for retesting after completion of automatic testing.

The aforementioned embodiment is to facilitate understanding of the invention. The aforementioned embodiment is not intended to limit the invention. It is obvious that the invention can be changed or improved without departing from the gist of the invention and any equivalent of the embodiment shall be included in the invention.

The display section 5 may be provided with a touch panel. In this case, the display section 5 can have a configuration in which when the user touches a position on the screen corresponding to at least one of the ten first symbols 511a, the ten second symbols 512a, the ten third symbols 513a, the ten fourth symbols 514a, the ten fifth symbols 515a, and the ten sixth symbols 516a, the display section 5 displays the detailed information 53 of the blood specimen contained in the blood collecting tube 10 corresponding to the symbol in the touched position.

According to such a configuration, user's operations can be integrated on the result screen 51. Accordingly, it is possible to further improve the efficiency of the work for specifying specimens required for retesting after completion of automatic testing.

As indicated by a dashed line in FIG. 3A, the hematology analyzer 1 may be further provided with a color sensor 6. The color sensor 6 is configured to be able to automatically identify the colors of the first rack 21, the second rack 22, the third rack 23, the fourth rack 24, the fifth rack 25 and the sixth rack 26.

For example, the respective racks are illuminated by blue, green and red lights emitted from light-emitting elements such as full color LEDs and intensity of each reflected light of the blue, green and red lights is measured by a light-detecting element such as a photodiode. Accordingly, the colors of the racks can be identified respectively. Alternatively, the color of each rack may be identified in such a manner that an identifier such as a barcode including information indicating the color of the rack is attached to the rack and the information is read by a suitable reading device.

In order to obtain the aforementioned result screen 51 without using the color sensor, the following configuration may be provided for example. A guidance color array consistent with the array of the respective colors of the first region 511, the second region 512, the third region 513, the fourth region 514, the fifth region 515 and the sixth region 516 is provided in advance on the carry-in section 2. The user can dispose the first rack 21, the second rack 22, the third rack 23, the fourth rack 24, the fifth rack 25 and the sixth rack 26 on the carry-in section 2 so as to obtain the color array designated by the guidance.

According to the configuration in which the color sensor is provided as described above, the user can be freed from the necessity of being aware of rules about the color array when the first rack 21, the second rack 22, the third rack 23, the fourth rack 24, the fifth rack 25 and the sixth rack 26 are disposed in the carry-in section 2. In addition, the degree of freedom for selecting the combination of the colors of the first rack 21, the second rack 22, the third rack 23, the fourth rack 24, the fifth rack 25 and the sixth rack 26 is enhanced. Accordingly, it is possible to improve not only the efficiency of the work of specifying specimens required for retesting after completion of automatic testing but also the efficiency of work performed prior to the start of the automatic testing.

Figure 5:
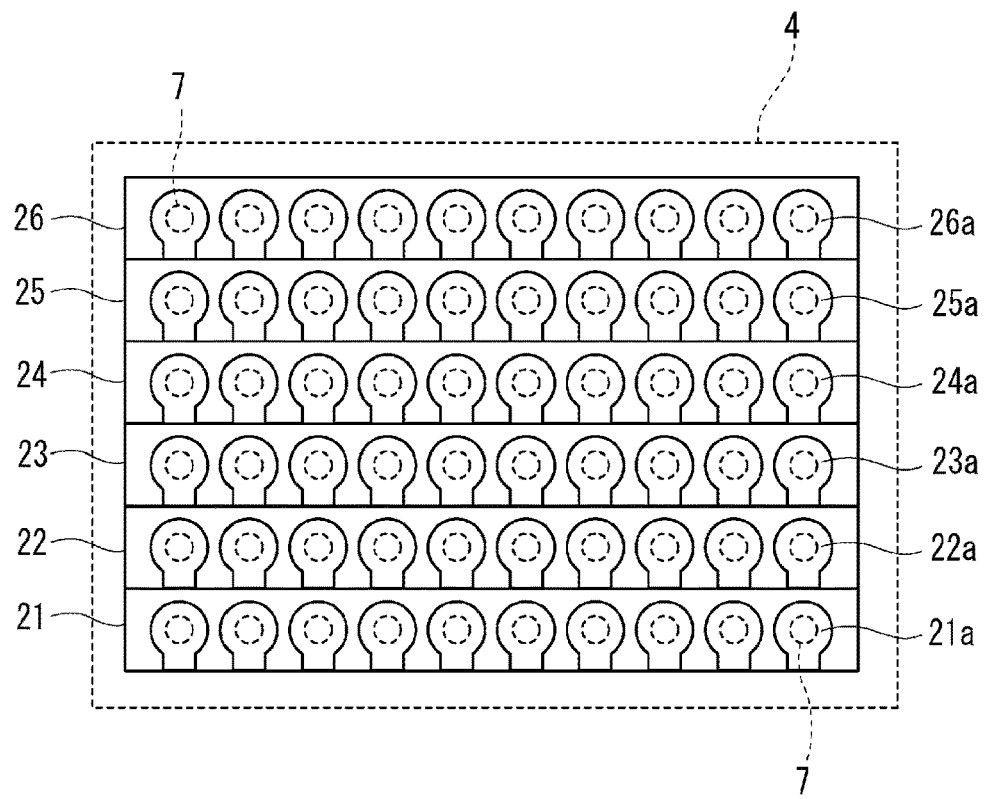
FIG. 5 schematically illustrates a part of a hematology analyzer according to one modified example.

As designated by broken lines in FIG. 5, the hematology analyzer 1 may be further provided with a plurality of light sources 7. In this case, each of the light sources 7 is disposed in a position where an associated one of the blood collecting tubes 10 can be illuminated. The light source 7 is configured to change its light emission state correspondingly to a test result performed by the test section 3.

For example, in the case where a test result indicates that a blood specimen falls out of a hematologic clinical criterion range (or a facility criterion range), the light source 7 corresponding to the position of the blood collecting tube 10 containing the blood specimen emits light. Configuration may be made in such a manner that the color of light emission changes in accordance with the kind of the test result (abnormality of the blood specimen, the measurement error, etc.).

In the case of the illustrated example, the light sources 7 are embedded in the carryout section 4 in advance. When the light sources 7 emit light, the blood collecting tubes 10 disposed above the light sources 7 are illuminated from below respectively.

According to such a configuration, for example, blood collecting tubes 10 containing blood specimens required for retesting can be illuminated by corresponding ones of the light sources 7. Accordingly, the user can specify the blood collecting tubes 10 easily. It is possible to further improve the efficiency of the work of specifying the specimens required for retesting after completion of automatic testing.

The light sources 7 may be provided in a separate light source unit from the carry-out section 4. The light source unit may take a form such as a basket for supporting the first rack 21, the second rack 22, the third rack 23, the fourth rack 24, the fifth rack 25 and the sixth rack 26.

In the aforementioned embodiment, configuration is made so that each of the first rack 21, the second rack 22, the third rack 23, the fourth rack 24, the fifth rack 25 and the sixth rack 26 can be held in a state that ten blood collecting tubes 10 are arranged side by side in a row in the first direction D1. When the number of arrays of blood collecting tubes 10 relevant to a specific color is only one, it is possible to minimize the burden of the judgment for specifying blood collecting tubes 10 containing blood specimens required for retesting based on the specific color. Accordingly, it is possible to further improve the efficiency of the work for specifying the specimens required for retesting after completion of automatic testing.

However, as long as there are a plurality of blood collecting tubes 10 which can be held in each rack, the number of the blood collecting tubes 10 may be determined appropriately. Examples of conceivable configurations may include a configuration in which five blood collecting tubes 10 arranged side by side in a row are held in the rack, a configuration in which twenty blood collecting tubes 10 arranged side by side in a row are held in the rack, a configuration in which twenty blood collecting tubes 10 arranged side by side in two rows each having ten blood collecting tubes 10 are held in the rack, etc.

In the aforementioned embodiment, the first rack 21, the second rack 22, the third rack 23, the fourth rack 24, the fifth rack 25 and the sixth rack 26 are arranged in the second direction D2 corresponding to the front/rear direction of the hematology analyzer 1. However, the first rack 21, the second rack 22, the third rack 23, the fourth rack 24, the fifth rack 25 and the sixth rack 26 may be disposed in the up/down direction of the hematology analyzer 1 as an example of the second direction D2 intersecting with the first direction D1. Alternatively, the first rack 21, the second rack 22, the third rack 23, the fourth rack 24, the fifth rack 25 and the sixth rack 26 may be disposed radially so that the first direction D1 can correspond to a radial direction of a circle and the second direction D2 can correspond to a circumferential direction of the circle.

In the aforementioned embodiment, six racks are used. As long as a plurality of racks are used, the number of racks to be provided for testing may be determined appropriately. It is preferable that the number of colors to be used is equal to the number of the racks.

Configuration may be made so that the carry-in section 2 can also serve as the carry-out section 4. That is, the hematology analyzer 1 may be configured so that the first rack 21, the second rack 22, the third rack 23, the fourth rack 24, the fifth rack 25 and the sixth rack 26 which have been tested by the test section 3 can be carried out to the carry-in section 2 again. In this case, it is possible to suppress the increase of the size of the hematology analyzer 1.

The present application is based on Japanese Patent Application No. 2015-098402 filed on May 13, 2015, the contents of which are hereby incorporated by reference.

What is claimed is:

1. A blood test apparatus comprising:
   a test section configured to perform a predetermined test with respect to blood specimens contained in a plurality of blood collecting tubes held by a first rack representing a first color and blood specimens contained in a plurality of blood collecting tubes held by a second rack representing a second color which is different from the first color;
   a carry-out section at which the first rack and the second rack are disposed after the test is finished; and
   a display section adjacent to the carry-out section and configured to display a result screen showing a result of the test,
   wherein the result screen includes:
   a first region displayed in a position corresponding to a position of the first rack in the carry-out section, and presenting the first color;
   a second region displayed in a position corresponding to a position of the second rack in the carry-out section, and presenting the second color;
   a plurality of first symbols displayed in the first region at positions corresponding to positions of the blood collecting tubes held in the first rack; and
   a plurality of second symbols displayed in the second region at positions corresponding to positions of the blood collecting tubes held in the second rack; and
   wherein a displayed appearance of each of the first symbols and the second symbols is changed in accordance with the result of the test.

2. The blood test apparatus of claim 1, further comprising a sensor configured to automatically recognize the first color and the second color.

3. The blood test apparatus of claim 1, wherein the display section is arranged adjacently to the carry-out section in an up-down direction of the blood test apparatus.

4. The blood test apparatus of claim 1, wherein the blood collecting test tubes held by the first rack and the blood collecting test tubes held by the second rack are arrayed in a first direction, and the carry-out section at which the first rack and the second rack are disposed is arranged in a second direction intersecting with the first direction after the test is finished.

5. The blood test apparatus of claim 1, wherein the result screen includes a plurality of first characters arranged in a first direction, and indicating test results of the blood specimens contained in the blood collecting tubes in the first rack and the second rack; and
   a plurality of second characters arranged in a second direction, and indicating positions of the first rack and the second rack.

6. The blood test apparatus of claim 1, wherein the carry-out section comprises a plurality of light sources.

7. The blood test apparatus of claim 6, wherein each of the plurality of light sources is associated with one of the blood collecting tubes.

8. The blood test apparatus of claim 1, wherein the result includes whether each of the blood specimens is normal or abnormal as well as a measurement error.

9. The blood test apparatus of claim 8, wherein the measurement error includes an error caused by a fault of the test section and an error caused by a fault of an identification information assigned to each of the blood collecting tubes.

10. The blood test apparatus of claim 1, wherein the display section is configured to hold a predetermined operation with respect to at least one of the first symbols and the second symbols, and to display detailed information of at least one blood specimen contained in at least one blood collecting tube corresponding to at least one symbol to which the predetermined operation is applied.

11. The blood test apparatus of claim 10, the display section comprising a touch panel,
wherein when a user touches at least one part of the touch panel corresponding to at least one of the first symbols and the second symbols, the display section displays detailed information of at least one blood specimen contained in at least one blood collecting tube corresponding to the at least one part that the user touched.

12. The blood test apparatus of claim 1, wherein each of the first rack and the second rack is configured to hold the blood collecting tubes such that the blood collecting tubes are arrayed in a first direction.

13. The blood test apparatus of claim 12, wherein the first rack and the second rack are arranged in a second direction intersecting with the first direction.

14. A blood test apparatus comprising:
a test section configured to perform a predetermined test with respect to blood specimens contained in a plurality of blood collecting tubes held by a first rack representing a first color and blood specimens contained in a plurality of blood collecting tubes held by a second rack representing a second color which is different from the first color;
a carry-out section at which the first rack and the second rack are disposed after the test is finished;
a display section configured to display a result screen showing a result of the test,
wherein the result test screen includes:
a first region displayed in a position corresponding to a position of the first rack in the carry-out section, and presenting the first color;
a second region displayed in a position corresponding to a position of the second rack in the carry-out section, and presenting the second color;
a plurality of first symbols displayed in the first region at positions corresponding to positions of the blood collecting tubes held in the first rack;
a plurality of second symbols displayed in the second region at positions corresponding to positions of the blood collecting tubes held in the second rack;
wherein a displayed appearance of each of the first symbols and the second symbols is changed in accordance with the result of the test;
wherein the carry-out section comprises a plurality of light sources;
wherein each of the light sources is disposed in a position capable of illuminating an associated one of the blood collecting tubes; and
wherein a light emitting condition of each of the light sources is changed in accordance with the result of the test.

* * * * *